(12) United States Patent  (10) Patent No.: US 7,538,244 B2
Ritter  (45) Date of Patent: *May 26, 2009

(54) PROCESS FOR THE SYNTHESIS OF HYDROXY AROMATIC ACIDS

(75) Inventor: Joachim C. Ritter, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 12/025,902

(22) Filed: Feb. 5, 2008

(65) Prior Publication Data

US 2008/0139843 A1   Jun. 12, 2008

Related U.S. Application Data

(62) Division of application No. 11/604,936, filed on Nov. 28, 2006, now Pat. No. 7,335,791.

(51) Int. Cl.
  *C07C 63/00* (2006.01)
(52) U.S. Cl. .................... 562/405; 562/400; 562/412
(58) Field of Classification Search ................ 562/405, 562/400
  See application file for complete search history.

(56) References Cited

U.S. PATENT DOCUMENTS

| 3,047,536 | A | 7/1962 | Gordon |
| 3,227,680 | A | 1/1966 | Tamblyn et al. |
| 3,894,079 | A | 7/1975 | Knobloch |
| 3,932,542 | A | 1/1976 | Gerns |
| 4,030,933 | A | 6/1977 | Conciatori |
| 5,674,969 | A | 10/1997 | Sikkema et al. |
| 5,703,264 | A | 12/1997 | Yoshida |
| 5,703,274 | A | 12/1997 | Gelmont et al. |
| 6,245,929 | B1 | 6/2001 | Soloveichik |

FOREIGN PATENT DOCUMENTS

| AT | 265 244 | 10/1968 |
| AU | 265244 | 5/1967 |
| GB | 1238224 | 7/1971 |
| IL | 112 706 | 4/1998 |
| WO | WO 2006/104974 | 10/2006 |

OTHER PUBLICATIONS

T.Singh, S.N.Bedi, Di-xanthones. Part I. Chromono-2':3'-2:3-xanthone, Jour.Indian Chem.Soc., 1957, vol. 34, No. 4, pp. 321-323.*
I. Rusonik, H.Cohen, D.Meyerstein, Cu(I)(2,5,8,11-tetramethyl-2,5,8,11-tetraazododecane) as a catalyst for Ullman's reaction, Dalton Transactions, 2003, 10, pp. 2024-2028.*
Zhang et al., "Amino Acid Promoted CuI-Catalyzed C-N Bond Formation Between Aryl Halides and Amines or N-Containing Heterocycles", J. Org. Chem., vol. 70, 2005, pp. 5164-5173.
PCT International Search Report and Written Opinion for International Application No. PCT/US2007/024466 dated Mar. 31, 2008.

U.S. Appl. No. 11/604,935, Ritter.
U.S. Appl. No. 11/604,936, Ritter.
U.S. Appl. No. 11/604,937, Ritter.
U.S. Appl. No. 11/604,938, Ritter.
U.S. Appl. No. 11/604,939, Ritter.
U.S. Appl. No. 11/604,940, Ritter.
U.S. Appl. No. 11/604,941, Ritter.
U.S. Appl. No. 11/604,942, Ritter.
U.S. Appl. No. 60/665,737, filed Mar. 28, 2005, Allen et al.
Adolf Marzin, 2,5-Dibromotoluic Acid, Journal Fur Praktische Chemie, 1933, vol. 138:103-106.
Tara Singh et. al., Di-Xanthones. Part I. Chromono-2':3'-2:3-Xanthone, Jour. Indian Chem. Soc., 1957, vol. 34(4):321-323.
Irena Rusonik et. al., CU(i)(2,5,8,11-Tetramethyl-2,5,8,11-Tetraazadodecane)+ as a Catalyst for Ullmann's Reaction, Dalton Trans., 2003, pp. 2024-2028.
Rolando F. Pellon Comdom et. al., Synthesis of Salicyclic Acid Derivatives from the Corresponding 2-Chlorobenzoic Acid Using Water as Solvent, Synthetic Communications, 2002, vol. 32(13):2055-2059.
Mark Gelmont et. al., A New Route for the Preparation of 5-Hydroxyisophthalic Acid, Organic Process Research & Development, 2002, vol. 6:591-596.
Yoel Sasson et. al., Liquid-Phase Oxidation of Deactivated Methylbenzenes by Aqueous Sodium Hypochlorite Catalyzed by Ruthenium Salts Under Phase-Transfer, Journal of Organic Chemistry, 1986, vol. 51:2880-2883.
Magal Saphier et al., Copper (i) as a Homogenous Catalyst for the Ullmann Reaction in Aqueous Solutions—The Transformation of 2-Bromobenzoate into Salicylate, Eur. J. Inorg. Chem., 2002, pp. 1226-1234.
J. E. McIntyre et. al., The Oxidation of Alkylaromatic Compounds in Aqueous Hydrogen Bromide., Journal of the Chemical Society, Abstracts, 1961, pp. 4082-4085.
F. F. Shcherbina et. al., Liquid-Phase Oxidation of 2,5-Dichloro-p-Xylene, Zhurnal Prikladnoi Khimil, Sankt-Peterburg, Russian Federation, 1990, vol. 63:467-470.
Robert J. Perry et. al., Synthesis of Polyimides via the Palladium-Catalyzed Carbonylation of Bis(O-Iodo Esters) and Diamines, Macromolecules, 1995, vol. 28:3509-3515.
Ruggli and Brandt, A New Linear Benzodipicoline, 2,6-Dimethyl-1,5-anthrazoline, 51st Communication Concerning Nitrogen Heterocycles, Basel University Institute for Organic Chemistry, Basel, Switzerland, Jan. 6, 1944.
Kevin W. Anderson et al, The Selective Reaction of Aryl Halides with KOH: Synthesis of Phenols, Aromatic Ethers, and Benzofurans; J. Am. Chem. Soc. 2006, 128, 10694-10695, American Chemical Society, New York NY.

(Continued)

*Primary Examiner*—Jafar Parsa
*Assistant Examiner*—Sudhakar Katakam

(57) ABSTRACT

Hydroxy aromatic acids are produced in high yields and high purity (>95%) from halogenated aromatic acids in a reaction mixture containing a copper source and a ligand that coordinates to copper.

20 Claims, No Drawings

OTHER PUBLICATIONS

M. Lammers et al, Mechanical Properties and Structural Transitions in the New Rigid-Rod Polymer Fibre PIPD ("M5") During the Manufacturing Process, Polymer, vol. 39, No. 24, 1998, 5999-6005, Elsevier, New York NY.

Doetze J. Sikkema, Design, Synthesis and Properties of a Novel Rigid Rod Polymer, PIPD or "M5": High Modulus and Tenacity Fibres with Substantial Compressive Strength, Polymer, vol. 39, No. 24, 1998, pp. 5981-5986, Elsevier, New York, NY.

Doetze J. Sikkema, Manmade Fibers One Hundred Years: Polymers and Polymer Design, Journal of Applied Polymer Science, vol. 83, 484-488, 2002, John WIley & Sons, Inc., New York NY.

* cited by examiner

PROCESS FOR THE SYNTHESIS OF HYDROXY AROMATIC ACIDS

This application is a division of and claims the benefit of U.S. application Ser. No. 11/604,936, filed Nov. 28, 2006 now U.S. Pat. No. 7,335,791, which by this reference is incorporated in its entirety as a part hereof for all purposes.

TECHNICAL FIELD

This invention relates to the manufacture of hydroxy aromatic acids, which are valuable for a variety of purposes such as use as intermediates or as monomers to make polymers.

BACKGROUND

Hydroxy aromatic acids are useful as intermediates and additives in the manufacture of many valuable materials including pharmaceuticals and compounds active in crop protection, and are also useful as monomers in the production of polymers. Salicylic acid (o-hydroxybenzoic acid), for example, is used in the manufacture of aspirin and has other pharmaceutical applications. Esters of p-hydroxybenzoic acid, known as "parabens", are used as food and cosmetic preservatives. P-hydroxybenzoic acid and 6-hydroxy-2-naphthoic acid are each used as a component of liquid crystalline polymers.

Various preparations of hydroxybenzoic acids, including 2,5-dihydroxyterephthalic acid ("DHTA"), are known. Marzin, in *Journal fuer Praktische Chemie*, 1933, 138, 103-106, teaches the synthesis of 2,5-dihydroxyterephthalic acid ("DHTA") from 2,5-dibromoterephthalic acid ("DBTA") in the presence of copper powder.

Singh et al, in *Jour. Indian Chem. Soc.*, Vol. 34, No. 4, pages 321-323 (1957), report the preparation of a product that includes DHTA by the condensation of DBTA with phenol in the presence of KOH and copper powder.

Rusonik et al, *Dalton Trans.*, 2003, 2024-2028, describe the transformation of 2-bromobenzoic acid into salicylic acid, benzoic acid, and diphenoic acid in a reaction catalyzed by Cu(I) in the presence of various ligands. A tertiary tetraamine minimizes the formation of diphenoic acid in use with Cu(I).

Comdom et al, *Synthetic Communications*, 32(13), 2055-59 (2002), describe a process for the synthesis of salicylic acids from 2-chlorobenzoic acids. Stoichiometric amounts of pyridine (0.5 to 2.0 moles per mole of 2-chlorobenzoic acid) are used such as at least 1.0 mole pyridine per mole 2-chlorobenzoic acid. Cu powder is used as a catalyst along with the pyridine.

Gelmont et al, *Organic Process Research & Development*, 6(5), 591-596 (2002), and U.S. Pat. No. 5,703,274, describe a process for the preparation of 5-hydroxyisophthalic acid by hydrolyzing 5-bromoisophthalic acid, mixtures of 5-bromoisophthalic acid, dibromoisophthalic acid isomers, and salts thereof in an aqueous alkaline solution in the presence of a copper catalyst at a temperature of 100 to 270° C.

Israeli Patent 112,706 discloses a process for the preparation of 4-hydroxyphthalic acid, and a mixture of 3- and 4-hydroxyphthalic acids, by hydrolyzing the corresponding bromophthalic acids in an aqueous alkaline solution in the presence of a copper catalyst at a temperature of 100 to 160° C. Examples of copper catalysts disclosed include Cu(0), CuCl, $CuCl_2$, $Cu_2O$, CuO, $CuBr_2$, $CuSO_4$, $Cu(OH)_2$, and copper (II) acetate.

The various prior art processes for making hydroxybenzoic acids are characterized by long reaction times, limited conversion resulting in significant productivity loss, or the need to run under pressure and/or at higher temperatures (typically 140 to 250° C.) to get reasonable rates and productivity. A need therefore remains for a process by which hydroxybenzoic acids can be produced economically; with low inherent operational difficulty; and with high yields and high productivity in small- and large-scale operation, and in batch and continuous operation.

SUMMARY

One embodiment of this invention provides a process for preparing a hydroxy aromatic acid that is described generally by the structure of Formula I

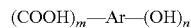

$(COOH)_m\text{—}Ar\text{—}(OH)_n$  I wherein Ar is a $C_6\text{~}C_{20}$ arylene radical, n and m are each independently a nonzero value, and n+m is less than or equal to 8, by (a) contacting a halogenated aromatic acid that is described generally by the structure of Formula II,

$(COOH)_m\text{—}Ar\text{—}(X)_n$  II wherein each X is independently Cl, Br or I, and Ar, n and m are as set forth above, with a base in water to form therefrom the corresponding m-basic salt of the halogenated aromatic acid in water; (b) contacting the m-basic salt of the halogenated aromatic acid with a base in water, and with a copper source in the presence of a ligand that coordinates to copper, to form the m-basic salt of a hydroxy aromatic acid from the m-basic salt of the halogenated aromatic acid at a solution pH of at least about 8,; (c) optionally, separating the m-basic salt of the hydroxy aromatic acid from the reaction mixture in which it is formed; and (d) contacting the m-basic salt of the hydroxy aromatic acid with acid to form therefrom a n-hydroxy aromatic acid.

In another embodiment, the ligand may be an amine ligand, the ratio of molar equivalents of ligand to molar equivalents of hydroxyl aromatic acid is less than or equal to about 0.1, and/or the ligand comprises, when it is a tetraamine, at least one primary or secondary amino group.

Yet another embodiment of this invention provides a process for preparing an n-alkoxy aromatic acid by preparing an n-hydroxy aromatic acid in the manner described above and then converting the n-hydroxy aromatic acid to an n-alkoxy aromatic acid.

Yet another embodiment of this invention consequently provides a process for preparing an n-alkoxy aromatic acid that is described generally by the structure of Formula VI

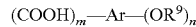

$(COOH)_m\text{—}Ar\text{—}(OR^9)_n$  VI wherein Ar is a $C_6\text{~}C_{20}$ arylene radical, each $R^9$ is independently a substituted or unsubstituted $C_{1\text{-}10}$ alkyl group, n and m are each independently a nonzero value, and n+m is less than or equal to 8, by (a) contacting a halogenated aromatic acid that is described generally by the structure of Formula II,

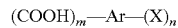

$(COOH)_m\text{—}Ar\text{—}(X)_n$  II wherein each X is independently Cl, Br or I, and Ar, n and m are as set forth above, with a base in water to form therefrom the corresponding m-basic salt of the halogenated aromatic acid in water; (b) contacting the m-basic salt of the halogenated aromatic acid with a base in water, and with a copper source in the presence of a ligand that coordinates to copper, to form the m-basic salt of a hydroxy aromatic acid from the m-basic salt of the halogenated aromatic acid at a solution pH of at least about 8; (c) optionally, separating the m-basic salt of the hydroxy aromatic acid from the reaction mixture in which it is formed; (d) contacting the m-basic salt of the hydroxy aromatic acid with acid to form therefrom an n-hydroxy aromatic acid that is described generally by the structure of Formula I, $$(COOH)_m\text{—}Ar\text{—}(OH)_n \qquad \qquad I$$

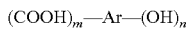

wherein Ar, n and m are as set forth above; and (e) converting the n-hydroxy aromatic acid to an n-alkoxy aromatic acid that is described generally by the structure of Formula VI, wherein Ar, $R^9$, n and m are as set forth above.

Yet another embodiment of this invention provides a process for preparing a 2,5-dihydroxyterephthalic acid or a 2,5-dialkoxyterephthalic acid as described above that further includes a step of subjecting the 2,5-dihydroxyterephthalic acid or the 2,5-dialkoxyterephthalic acid to a reaction to prepare therefrom a compound, monomer, oligomer or polymer.

Yet another embodiment of this invention consequently provides a process for preparing a compound, monomer, oligomer or polymer by preparing a hydroxy aromatic acid that is described generally by the structure of Formula I $$(COOH)_m\text{—}Ar\text{—}(OH)_n \qquad \qquad I$$

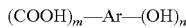

wherein Ar is a $C_6$–$C_{20}$ arylene radical, n and m are each independently a nonzero value, and n+m is less than or equal to 8, by (a) contacting a halogenated aromatic acid that is described generally by the structure of Formula II, $$(COOH)_m\text{—}Ar\text{—}(X)_n \qquad \qquad II$$

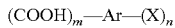

wherein each X is independently Cl, Br or I, and Ar, n and m are as set forth above, with a base in water to form therefrom the corresponding m-basic salt of the halogenated aromatic acid in water; (b) contacting the m-basic salt of the halogenated aromatic acid with a base in water, and with a copper source in the presence of a ligand that coordinates to copper, to form the m-basic salt of a hydroxy aromatic acid from the m-basic salt of the halogenated aromatic acid at a solution pH of at least about 8,; (c) optionally, separating the m-basic salt of the hydroxy aromatic acid from the reaction mixture in which it is formed; (d) contacting the m-basic salt of the hydroxy aromatic acid with acid to form therefrom an n-hydroxy aromatic acid; (e) optionally, converting the n-hydroxy aromatic acid to a n-alkoxy aromatic acid; and (f) subjecting the n-hydroxy aromatic acid and/or the n-alkoxy aromatic acid to a reaction to prepare therefrom a compound, monomer, oligomer or polymer.

DETAILED DESCRIPTION

This invention provides a high yield and high productivity process for preparing a hydroxy aromatic acid as described generally by the structure of Formula I $$(COOH)_m\text{—}Ar\text{—}(OH)_n \qquad \qquad I$$

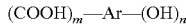

by contacting a halogenated aromatic acid as described generally by the structure of Formula II $$(COOH)_m\text{—}Ar\text{—}(X)_n \qquad \qquad II$$

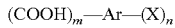

with base to form the m-basic salt of the halogenated aromatic acid; contacting the m-basic salt of the halogenated aromatic acid with base, and with a copper source in the presence of a ligand that coordinates to copper, to form the m-basic salt of an n-hydroxy aromatic acid; and then contacting the dibasic salt of the n-hydroxy aromatic acid with acid to form the n-hydroxy aromatic acid product.

In both Formulae I and II, Ar is a $C_6$–$C_{20}$ arylene radical, n and m are each independently a nonzero value, and n+m is less than or equal to 8; and in Formula II, each X is independently Cl, Br or I. The arylene radical denoted by "—Ar—" is a multi-valent aromatic radical formed by the removal of two or more hydrogens from different carbon atoms on the aromatic ring, or on the aromatic rings when the structure is multicyclic. There is consequently, for example, the possibility in the arylene radical that hydrogens may be removed from two up to all six carbon atoms on a benzyl ring, or hydrogens may be removed from any two and up to eight positions on either one or both rings of a naphthyl radical.

The arylene radical, "Ar", may be substituted or unsubstituted. The arylene radical, when unsubstituted, is a univalent group containing only carbon and hydrogen. In the arylene radical, however, one or more O or S atoms may optionally be substituted for any one or more of the in-chain or in-ring carbon atoms, provided that the resulting structure contains no —O—O— or —S—S— moieties, and provided that no carbon atom is bonded to more than one heteroatom. One example of a suitable arylene radical is phenylene, as shown below.

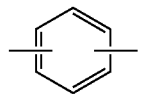

An "m-basic salt", as the term is used herein, is the salt formed from an acid that contains in each molecule m acid groups having a replaceable hydrogen atom.

Various halogenated aromatic acids, to be used as a starting material in the process of this invention, are commercially available. For example, 2-bromobenzoic acid is available from Aldrich Chemical Company (Milwaukee, Wis.). It can be synthesized, however, by oxidation of bromomethylbenzene as described in Sasson et al, *Journal of Organic Chemistry* (1986), 51(15), 2880-2883. Other halogenated aromatic acids that can be used include without limitation 2,5-dibromobenzoic acid, 2-bromo-5-nitrobenzoic acid, 2-bromo-5-methylbenzoic acid, 2-chlorobenzoic acid, 2,5-dichlorobenzoic acid, 2-chloro-3,5-dinitrobenzoic acid, 2-chloro-5-methylbenzoic acid, 2-bromo-5-methoxybenzoic acid, 5-bromo-2-chlorobenzoic acid, 2,3-dichlorobenzoic acid, 2-chloro-4-nitrobenzoic acid, 2,5-dichloroterephthalic acid, and 2-chloro-5-nitrobenzoic acid, all of which are commercially available.

Other halogenated aromatic acids useful as a starting material in the process of this invention include those shown in the left column of the table below, wherein X=Cl, Br or I, and wherein the corresponding hydroxy aromatic acid produced therefrom by the process of this invention is shown in the right column:

| I<br>$(COOH)_m$-Ar-$(X)_n$ | II<br>$(COOH)_m$-Ar-$(OH)_n$ |
|---|---|

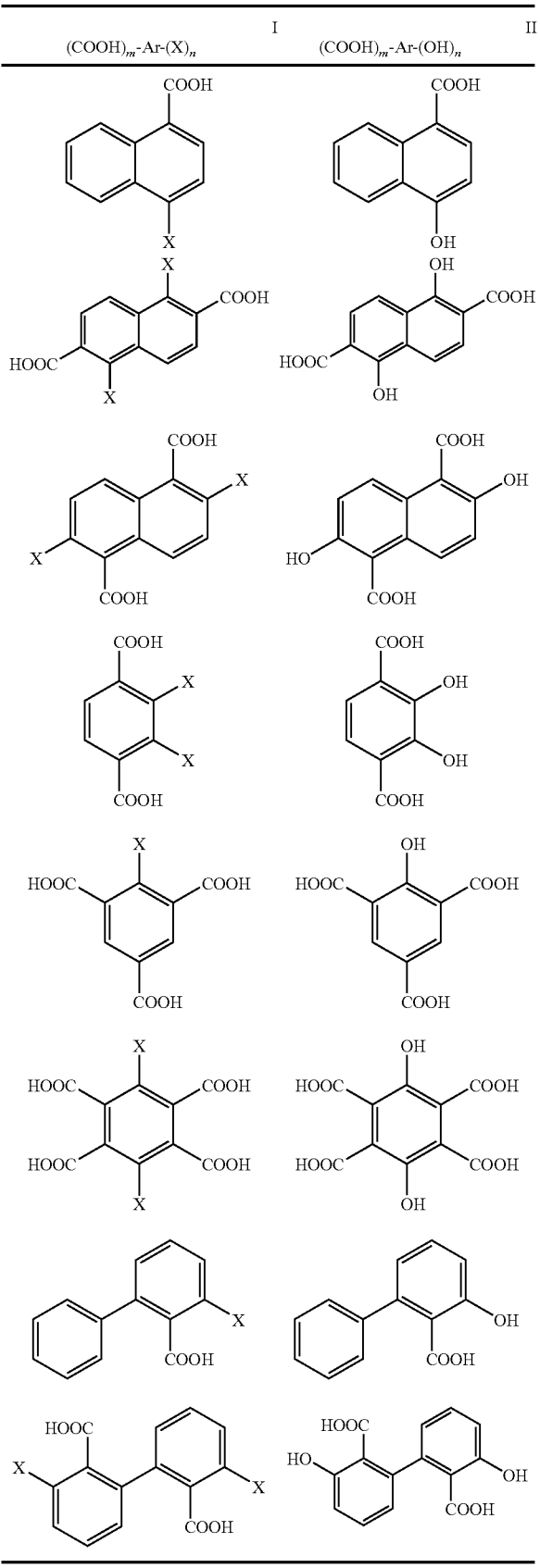

In step (a), a halogenated aromatic acid is contacted with base in water to form therefrom the corresponding m-basic salt of the halogenated aromatic acid. In step (b), the m-basic salt of the halogenated aromatic acid is contacted with base in water, and with a copper source in the presence of a ligand that coordinates to copper, to form the m-basic salt of a hydroxy aromatic acid from the m-basic salt of the halogenated aromatic acid.

The base used in step (a) and/or step (b) may be an ionic base, and may in particular be one or more of a hydroxide, carbonate, bicarbonate, phosphate or hydrogen phosphate of one or more of Li, Na, K, Mg or Ca. The base used may be water-soluble, partially water-soluble, or the solubility of the base may increase as the reaction progresses and/or as the base is consumed. NaOH and $Na_2CO_3$ are preferred, but other suitable organic bases may be selected, for example, from the group consisting of trialkylamines (such as tributylamine); N,N,N',N'-tetramethylethylenediamine; and N-alkyl imidazoles (for example, N-methylimidazole). In principle any base capable of maintaining a pH above 8 and/or binding the acid produced during the reaction of the halogenated aromatic acid is suitable.

The specific amounts of base to be used in steps (a) and/or (b) depend on the strength of the base. In step (a), a halogenated aromatic acid is preferably contacted with at least about m equivalents of water-soluble base per equivalent of halogenated aromatic acid. One "equivalent" as used for a base in this context is the number of moles of base that will react with one mole of hydrogen ions; for an acid, one equivalent is the number of moles of acid that will supply one mole of hydrogen ions.

In step (b), enough base should be used to maintain a solution pH of at least about 8, or at least about 9, or at least about 10, and preferably between about 9 and about 11. Thus, typically in step (b), the dibasic salt of the halogenated aromatic acid is contacted with at least about n equivalents of base, such as a water-soluble base, per equivalent of the m-basic salt of the halogenated aromatic acid.

In alternative embodiments, however, it may be desirable in steps (a) and (b) to use a total of at least about n+m+1 equivalents of base, such as a water-soluble base, in the reaction mixture per equivalent of the halogenated aromatic acid originally used at the start of the reaction. A base used in an amount as described above is typically a strong base, and is typically added at ambient temperature. The base used in step (b) may be the same as, or different than, the base used in step (a).

As mentioned above, in step (b), the m-basic salt of the halogenated aromatic acid is also contacted with a copper source in the presence of a ligand that coordinates to copper. The copper source and the ligand may be added sequentially to the reaction mixture, or may be combined separately (for example, in a solution of water or acetonitrile) and added together. The copper source may be combined with the ligand in the presence of oxygen in water, or be combined with a solvent mixture containing water.

From the presence together in the reaction mixture of the copper source and the ligand, in a basic solution of the m-basic salt of the halogenated aromatic acid, there is obtained an aqueous mixture containing the m-basic salt of a hydroxy aromatic acid, copper specie(s), the ligand, and a halide salt. If desired, the m-basic salt of the hydroxy aromatic acid may, at this stage and before the acidification in step (d), be separated from the mixture [as optional step (c)], and may be used as an m-basic salt in another reaction or for other purposes.

The m-basic salt of the hydroxy aromatic acid is then contacted in step (d) with acid to convert it to the hydroxy aromatic acid product. Any acid of sufficient strength to protonate the m-basic salt is suitable. Examples include without limitation hydrochloric acid, sulfuric acid and phosphoric acid.

The reaction temperature for steps (a) and (b) is preferably between about 40 and about 120° C., more preferably between about 75 and about 95° C.; and the process thus in various embodiments involves a step of heating the reaction mixture. The solution is typically allowed to cool before the acidification in step (d) is carried out. In various embodiments, oxygen may be excluded during the reaction.

The copper source is copper metal ["Cu(0)"], one or more copper compounds, or a mixture of copper metal and one or more copper compounds. The copper compound may be a Cu(I) salt, a Cu(II) salt, or mixtures thereof. Examples include without limitation $CuCl$, $CuBr$, $CuI$, $Cu_2SO_4$, $CuNO_3$, $CuCl_2$, $CuBr_2$, $CuI_2$, $CuSO_4$, and $Cu(NO_3)_2$. The selection of the copper source may be made in relation to the identity of the halogenated aromatic acid used. For example, if the starting halogenated aromatic acid is a bromobenzoic acid, $CuCl$, $CuBr$, $CuI$, $Cu_2SO_4$, $CuNO_3$, $CuCl_2$, $CuBr_2$, $CuI_2$, $CuSO_4$, and $Cu(NO_3)_2$ will be included among the useful choices. If the starting halogenated aromatic acid is a chlorobenzoic acid, $CuBr$, $CuI$, $CuBr_2$ and $CuI_2$ will be included among the useful choices. $CuBr$ and $CuBr_2$ are in general preferred choices for most systems. The amount of copper used is typically about 0.1 to about 5 mol % based on moles of halogenated aromatic acid.

When the copper source is Cu(0), Cu(0), copper bromide and a ligand may be combined in the presence of air. In the case of Cu(0) or Cu(I), a predetermined amount of metal and ligand may be combined in water, and the resulting mixture may be reacted with air or dilute oxygen until a colored solution is formed. The resulting metal/ligand solution is added to the reaction mixture containing the m-basic salt of the halogenated aromatic acid and base in water.

The ligand may be a straight- or branched-chain or cyclic, aliphatic or aromatic, substituted or unsubstituted, amine, or a mixture of two of more such ligands. Whether formed as a compound, an oligomer or polymer, conventional nomenclature may be used to describe the number of amine groups present in the ligand, such as a mono-, di-, tri-, tetra-, penta-, hexa-, hepta- or octaamine, and so on. In its unsubstituted form, the ligand may be an organoamine that contains carbon, nitrogen and hydrogen atoms only. In it substituted form, the amine ligand may contain hetero atoms such as oxygen or sulfur. In various embodiments, particularly but not exclusively as relates to the tetramines, the amine may contain at least one primary or secondary amino group.

Primary or secondary monoamines suitable for use herein as the ligand include those described generally by the following Formula 11

11 wherein $R^1$ and $R^2$ are each independently selected from
H;
a $C_1$~$C_{10}$ straight-chain or branched, saturated or unsaturated, substituted or unsubstituted, hydrocarbyl radical;
a $C_3$~$C_{12}$ cyclic aliphatic, saturated or unsaturated, substituted or unsubstituted, hydrocarbyl radical; or
a $C_6$~$C_{12}$ aromatic substituted or unsubstituted hydrocarbyl radical.

In certain embodiments, $R^1$ and/or $R^2$ may for example be a methyl, ethyl, propyl, butyl, pentyl, hexyl or phenyl radical. In other embodiments, at least one of $R^1$ and $R^2$ is not H. Particular monoamines suitable for use herein as the ligand include ethyl amine, isopropylamine, sec-butyl amine, dimethyl amine, methyl ethyl amine, ethyl-n-butyl amine, allylamine, cyclohexyl amine, N-ethylcyclohexyl amine, aniline, N-ethyl aniline, toluidine and xylidine.

Primary or secondary diamines suitable for use herein as the ligand include those described generally by the following Formula 12

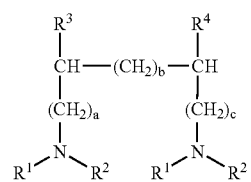

12 wherein each $R^1$ and each $R^2$ is independently
H;
a $C_1$~$C_{10}$ straight-chain or branched, saturated or unsaturated, substituted or unsubstituted, hydrocarbyl radical;
a $C_3$~$C_{12}$ cyclic aliphatic, saturated or unsaturated, substituted or unsubstituted, hydrocarbyl radical; or
a $C_6$~$C_{12}$ aromatic substituted or unsubstituted hydrocarbyl radical;

wherein $R^3$ and $R^4$ are each independently
H;
a $C_1$~$C_{10}$ straight-chain or branched, saturated or unsaturated, substituted or unsubstituted, hydrocarbyl radical;
a $C_3$~$C_{12}$ cyclic aliphatic, saturated or unsaturated, substituted or unsubstituted, hydrocarbyl radical; or
a $C_6$~$C_{12}$ aromatic substituted or unsubstituted hydrocarbyl radical; or $R^3$ and $R^4$ are joined to form a ring structure that is
a $C_4$~$C_{12}$ aliphatic, saturated or unsaturated, substituted or unsubstituted, hydrocarbyl ring structure; or
a $C_6$~$C_{12}$ aromatic substituted or unsubstituted hydrocarbyl ring structure; and wherein a, b, and c are each independently 0~4.

In certain embodiments, one or both of the $R^1$s is H. In other embodiments, one or both of the $R^2$S is also H. In other embodiments, any one or more of $R^1$ to $R^4$ may be a methyl, ethyl, propyl, butyl, pentyl, hexyl or phenyl radical.

In various particular embodiments, a, b and c may all equal 0, and either $R^3=R^4=H$, or $R^3$ and $R^4$ are joined to form an aliphatic ring structure. Particularly when b=0, the aliphatic ring structure may be a cyclohexylene group, which is the divalent radical, —$C_6H_{10}$—, as shown below, thus providing a cyclohexyl diamine:

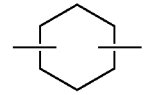

The formation of a cyclohexylene group from $R^3$ and $R^4$ may be illustrated generally by the following structure:

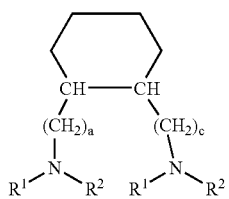

where $R^1$, $R^2$, a and c are as set forth above. In alternative embodiments, however, one amino group, or the alkyl radical on which it is located, may be in the meta or para position on the cycloalkyl or aromatic ring to the other amino group.

Suitable aliphatic diamines may include N,N'-di-n-alkylethylene diamines and N,N'-di-n-alkylcyclohexane-1,2-diamines. Specific examples include without limitation N,N'-dimethylethylene diamine, N,N'-diethylethylene diamine, N,N'-di-n-propylethylene diamine, N,N'-dibutylethylene diamine, N,N'-dimethylcyclohexane-1,2-diamine, N,N'-diethylcyclohexane-1,2-diamine, N,N'-di-n-propylcyclohexane-1,2-diamine, and N,N'-dibutylcyclohexane-1,2-diamine. Examples of suitable aromatic diamines include without limitation 1,2-phenylenediamine and N,N'-dialkylphenylene diamines such as N,N'-dimethyl-1,2-phenylenediamine and N,N'-diethyl-1,2-phenylenediamine; and benzidine.

Primary or secondary tri- and higher amines suitable for use herein as the ligand may be described generally by the following Formula 13:

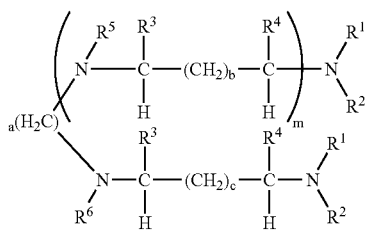

13 wherein each $R^1$, $R^2$, $R^3$, $R^4$, $R^5$ and $R^6$ is independently selected from;

H;

a $C_1\sim C_{10}$ straight-chain or branched, saturated or unsaturated, substituted or unsubstituted, hydrocarbyl radical;

a $C_3\sim C_{12}$ cyclic aliphatic, saturated or unsaturated, substituted or unsubstituted, hydrocarbyl radical; or a $C_6\sim C_{12}$ aromatic substituted or unsubstituted hydrocarbyl radical; and wherein a is 2~4, b and c is each independently 0~4; and m>0.

In certain embodiments, one or both of the $R^1$s, or at least one $R^3$, or at least one $R^4$, or $R^5$, and/or $R^6$ is H. In other particular embodiments, m=0, 1, 2, 3, 4 or 5. In yet other embodiments, $R^3=R^4=R^5=H$; and/or one or both of $R^1$ and $R^2=H$. In further embodiments, any one or more of $R^1$ through $R^6$ may be a methyl, ethyl, propyl, butyl, pentyl, hexyl or phenyl radical.

Amines according to Formula 13 suitable for use herein as the ligand include, for example, those described generally by the following Formula 14:

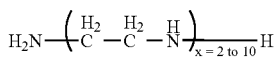

wherein x is 2~10. Formula 14 describes various polyethyleneamines where, in Formula 13, each R group is H, a=2, b=c=0, and m=0 to 8.

Other amines according to Formula 13, or other higher amines, suitable for use herein as the ligand include diethylenetriamine and triethylenetetramine, as well as those described generally by the following structures:

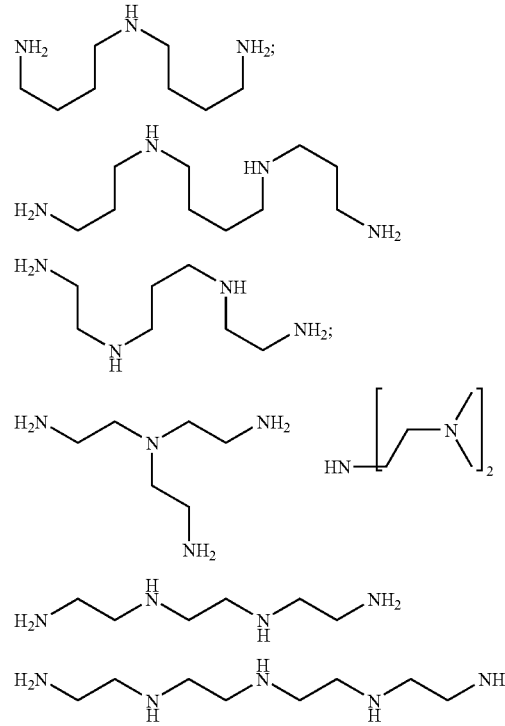

The ligand may also be a cyclic amine compound that is a molecule having at least one closed ring structure in which at least one ring atom is nitrogen. This form of ligand is then heterocyclic in the sense that the ring structure will contain, in addition to nitrogen atoms, other atoms that are primarily carbon and hydrogen, but may also be oxygen and/or sulfur, as described below. The nitrogen atom may for example be a member of a $C_4\sim C_{12}$ aliphatic, saturated or unsaturated, substituted or unsubstituted hydrocarbyl ring structure; or a $C_5\sim C_{12}$ aromatic, substituted or unsubstituted hydrocarbyl ring structure.

Examples of various nitrogen-containing, cyclic compounds suitable for use herein as the ligand include without limitation quinolione, indole, imidazole, ethylenimine, as well as those described by the following structures:

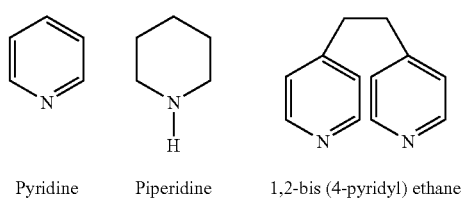

Pyridine     Piperidine     1,2-bis (4-pyridyl) ethane

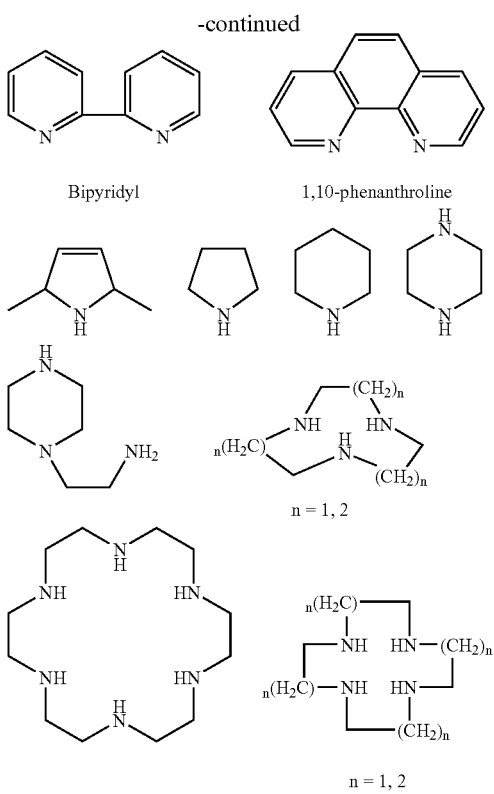
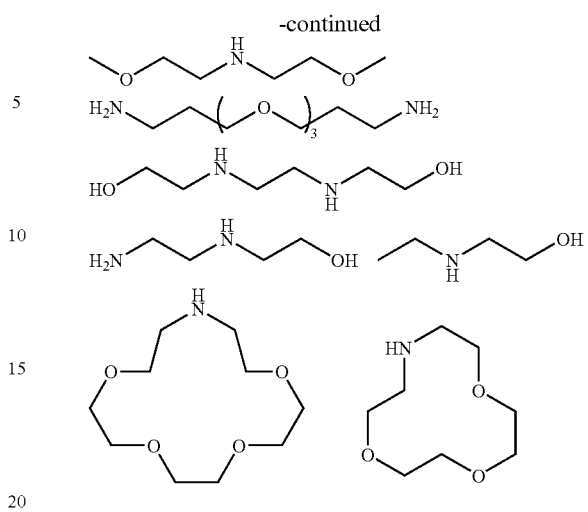

The "hydrocarbyl" groups referred to above in the descriptions of ligands suitable for use herein are, when unsubstituted, univalent groups containing only carbon and hydrogen. Similarly, an unsubstituted amine is a compound that contains in its structure nitrogen, carbon and hydrogen atoms only. In any of the hydrocarbyl radicals or ring structures described above, however, one or more O or S atoms may optionally be substituted for any one or more of the in-chain or in-ring carbon atoms, provided that the resulting structure contains no —O—O— or —S—S— moieties, and provided that no carbon atom is bonded to more than one heteroatom. An example of a suitable ligand in which an oxygen atom has been substituted for a carbon atom is shown in Formula 15:

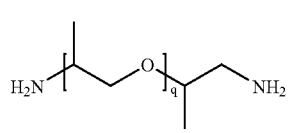

wherein q may have, for example, an average value of about 3 in a mixture of molecules with different molecular weights.

Other examples of ligands suitable for use herein and having oxygen substitution include anisidine, phenetidine, as well as those described generally by the following structures:

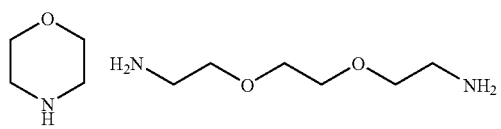

Ligands of particular versatility include secondary amines, particularly N,N'-substituted 1,2-diamines, including those that that may be described as $R^7NH$—$(CHR^8CHR^9)$—$NHR^{10}$ wherein $R^7$ and $R^{10}$ are each independently chosen from the group of $C_1$-$C_4$ primary alkyl radicals, and $R^8$ and $R^9$ are each independently chosen from the group of H and $C_1$-$C_4$ alkyl radicals, and/or where $R^8$ and $R^9$ may be joined to form a ring structure.

When, in Formula 12, $R^3$ and $R^4$ are joined to form an aromatic ring structure, and/or when a cyclic amine ligand contains one or more aromatic ring structures, more severe reaction conditions (e.g. higher temperature, or larger amounts of copper and/or ligand) may be needed to achieve high conversion, selectivity, yield and/or purity in the reaction.

A ligand suitable for use herein may be selected as any one or more or all of the members of the whole population of ligands described by name or structure above. A suitable ligand may, however, also be selected as any one or more or all of the members of a subgroup of the whole population, where the subgroup may be any size (1, 2, 6, 10 or 20, for example), and where the subgroup is formed by omitting any one or more of the members of the whole population as described above. As a result, the ligand may in such instance not only be selected as one or more or all of the members of any subgroup of any size that may be formed from the whole population of ligands as described above, but the ligand may also be selected in the absence of the members that have been omitted from the whole population to form the subgroup. For example, in certain embodiments, the ligand useful herein may be selected as one or more or all of the members of a subgroup of ligands that excludes from the whole population pyridine, 2,5,8,11-tetramethyl-2,5,8,11-tetraazadodecane, and/or 1,1,4,7,10,10-hexamethyltriethylenetetraamine, with or without the exclusion from the whole population of other ligands too.

In various embodiments, the ligand may be provided in an amount of about 1 to about 8, preferably about 1 to about 2, molar equivalents of ligand per mole of copper. In those and other embodiments, the ratio of molar equivalents of ligand to molar equivalents of halogenated aromatic acid may be less than or equal to about 0.1. As used herein, the term "molar equivalent" indicates the number of moles of ligand that will interact with one mole of copper.

In one embodiment, a Cu(I) salt may be selected as CuBr; the ligand is selected from the group consisting of N,N'-dimethylethylene diamine, N,N'-diethylethylene diamine, N,N'-di-n-propylethylene diamine, N,N'-dibutylethylene diamine, N,N'-dimethylcyclohexane-1,2-diamine, N,N'-diethylcyclohexane-1,2-diamine, N,N'-di-n-propylcyclohexane-1,2-diamine, N,N'-dibutylcyclohexane-1,2-diamine; and CuBr is combined with two molar equivalents of the ligand in the presence of water and air.

The ligand is believed to facilitate the action of the copper source as a catalyst, and/or the copper source and the ligand are believed to function together to act as a catalyst, to improve one or more attributes of the reaction.

The process described above also allows for effective and efficient synthesis of related compounds, such as n-alkoxy aromatic acids, which may be described generally by the structure of Formula VI:

$(COOH)_m—Ar—(OR^9)_n$      VI wherein Ar, m and n are described as set forth above, and each $R^9$ is independently a substituted or unsubstituted $C_{1-10}$ alkyl group. An $R^9$ is, when unsubstituted, a univalent group containing only carbon and hydrogen. In any such alkyl group, however, one or more O or S atoms may optionally be substituted for any one or more of the in-chain carbon atoms, provided that the resulting structure contains no —O—O— or —S—S— moieties, and provided that no carbon atom is bonded to more than one heteroatom.

An n-hydroxy aromatic acid, as prepared by the process of this invention, may be converted to an n-alkoxy aromatic acid, and such conversion may be accomplished, for example, by contacting the hydroxy aromatic acid under basic conditions with an n-alkyl sulfate of the formula $(R^9)_nSO_4$. One suitable method of running such a conversion reaction is as described in Austrian Patent No. 265,244. Suitable basic conditions for such conversion are a solution pH of at least about 8, or at least about 9, or at least about 10, and preferably about 9 to about 11, using one or more bases such as described above.

In certain embodiments, it may be desired to separate the n-hydroxy aromatic acid from the reaction mixture in which it was formed before converting it to an n-alkoxy aromatic acid.

The process described above also allows for effective and efficient synthesis of products made from the resulting 2,5-dihydroxyterephthalic acid or 2,5-dialkoxyterephthalic acid such as a compound, a monomer, or an oligomer or polymer thereof. These produced materials may have one or more of ester functionality, ether functionality, amide functionality, imide functionality, imidazole functionality, carbonate functionality, acrylate functionality, epoxide functionality, urethane functionality, acetal functionality, and anhydride functionality.

Representative reactions involving a material made by the process of this invention, or a derivative of such material, include, for example, making a polyester from a 2,5-dihydroxyterephthalic acid and either diethylene glycol or triethylene glycol in the presence of 0.1% of $ZN_3(BO_3)_2$ in 1-methylnaphthalene under nitrogen, as disclosed in U.S. Pat. No. 3,047,536 (which is incorporated in its entirety as a part hereof for all purposes). Similarly, a 2,5-dihydroxyterephthalic acid is disclosed as suitable for copolymeriztion with a dibasic acid and a glycol to prepare a heat-stabilized polyester in U.S. Pat. No. 3,227,680 (which is incorporated in its entirety as a part hereof for all purposes), wherein representative conditions involve forming a prepolymer in the presence of titanium tetraisopropoxide in butanol at 200~250° C., followed by solid-phase polymerization at 280° C. at a pressure of 0.08 mm Hg.

A 2,5-dihydroxyterephthalic acid has also been polymerized with the trihydrochloride-monohydrate of tetraaminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665,737, filed Mar. 28, 2005 (which is incorporated in its entirety as a part hereof for all purposes), published as WO 2006/104974. The polymer that may be so produced may be a pyridobisimidazole-2,6-diyl(2,5-dihydroxy-p-phenylene) polymer such as a poly(1,4-(2,5-dihydroxy)phenylene-2,6-pyrido[2,3-d: 5,6-d'] bisimidazole) polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replace the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials. All reagents were used as received. The ligands listed in Table 1 (labeled A through O, and R) were obtained from Aldrich Chemical Company (Milwaukee, Wis.). Ligand P was obtained from TCI America (Portland, Oreg.).

TABLE 1

| Ligand Code | Ligand | Purity (%) |
|---|---|---|
| A | N,N-Dimethylethylenediamine | 95 |
| B | N,N'-Diethylethylenediamine | 95 |
| C | N,N'-Dimethyl-1,6-hexanediamine | 98 |
| D | N,N-Diethyl-N'-methyethylenediamine | 97 |
| E | 1,2-Phenylenediamine | 98 |

TABLE 1-continued

| Ligand Code | Ligand | Purity (%) |
|---|---|---|
| F | rac-trans-N,N'-Dimethylcyclohexane-1,2-diamine | 97 |
| G | N-Methylethylenediamine | 95 |
| H | 1,2-Bis(4-pyridyl)ethane | 99 |
| I | N,N,N',N'-tetramethylethylenediamine | 99 |
| J | rac 1,2-Diaminocyclohexane | 99 |
| K | N,N'-Dimethylethylenediamine | 99 |
| L | 1,10-Phenanthroline | 99+ |
| M | Ethylenediamine diacetate | 98 |
| N | N,N'-Diisopropylethylene diamine | 99 |
| O | 1,1,4,7,10,10-Hexamethyltriethylenetetramine | 97 |
| P | (1S,2S)-(+)-Dimethylcyclohexane-1,2-diamine | 95 |
| R | Bipyridyl | >99 |

2-bromobenzoic acid (97% purity), 2,5-dibromobenzoic acid (96% purity), 2-bromo-5-nitrobenzoic acid (98% purity), 4-bromobenzoic acid (98% purity), 4-chlorobenzoic acid (99% purity), 2,4-dichloro benzoic acid (98% purity), 2,5-dichloro benzoic acid (97% purity), 2-chloro-5-nitro benzoic acid (97% purity), 2-bromo-5-methoxy benzoic acid (98% purity) and 5-bromo-2-chloro benzoic acid (98% purity), were obtained from Aldrich Chemical Company (Milwaukee, Wis.).

2,5-dibromoterephthalic acid (95+% purity) was obtained from Maybridge Chemical Company Ltd. (Cornwall, United Kingdom). 2-bromo-5-methyl benzoic acid and 2-chloro-5-methylbenzoic acid (98% purity) were obtained from Oakwood Products, Inc. (West Columbia, S.C., USA). 2-chloro-3,5-dinitrobenzoic acid (97% purity) was obtained from Avocado Organics(now part of Alfa Aesar, a Johnson-Matthey Company, Ward Hill, Mass., USA).

Copper(I) bromide ("CuBr") (98%) and copper(II) bromide ("CuBr$_2$") were obtained from Acros Organics (Geel, Belgium). Copper(II) sulfate ("CuSO$_4$") (98% purity) was obtained from Strem Chemicals, Inc. (Newburyport, Mass., USA).

Acetonitrile (99.8%) and Na$_2$CO$_3$ (99.5%) were obtained from EM Science (Gibbstown, N.J.).

As used herein, the term "conversion" refers to how much reactant was used up as a fraction or percentage of the theoretical amount. The term "selectivity" for a product P refers to the molar fraction or molar percentage of P in the final product mix. The conversion multiplied by the selectivity thus equals the maximum "yield" of P; the actual or "net" yield will normally be somewhat less than this because of sample losses incurred in the course of activities such as isolating, handling, drying, and the like. The term "purity" denotes what percentage of the in-hand, isolated sample is actually the specified substance.

The terms "15% HCl" as used in the Examples denotes aqueous hydrochloric acid whose concentration is 15 grams of HCl per 100 mL of solution. Similarly, "35% HCl" denotes aqueous hydrochloric acid whose concentration is 35 grams of HCl per 100 mL of solution. The terms "H$_2$O" and "water" as used in the Examples refer to distilled water. Product purity was determined by $^1$H NMR.

The meaning of abbreviations is as follows "h" means hour(s), "min" means minute(s), "mL" means milliliter(s), "g" means gram(s), "mg" means milligram(s), "mmol" means millimole(s), "M" means molar, "NMR" means nuclear magnetic resonance spectroscopy, "CONV" means conversion (percent), "SEL" means selectivity (percent), "T" means temperature, and "t" means time.

Example 1

Under nitrogen, 2.00 g (9.95 mmol) of 2-bromobenzoic acid was combined with 10 g of H$_2$O. 1.11 g (10.45 mmol) of Na$_2$CO$_3$ was then added. The mixture was heated to reflux with stirring for 30 min, remaining under a nitrogen atmosphere. Another 1.58 g (14.92 mmol) of Na$_2$CO$_3$ was added to the reaction mixture and reflux was continued for 30 min. Separately, 22 mg of CuBr$_2$ and 28 mg of rac-trans-N,N'-dimethylcyclohexane-1,2-diamine (Ligand F) were combined with 2 mL H$_2$O under nitrogen to give a deep purple solution. This solution was added to the stirred reaction mixture via syringe at 80° C. under nitrogen and stirred for 1 h at 80° C. After cooling to 25° C., the reaction mixture was acidified with 15% HCl, producing a white precipitate. The white precipitate was filtered and washed with water. After drying, a total of 1.34 g (9.7 mmol, 98% yield) salicylic acid was collected. The purity was determined by $^1$H NMR to be about 99%.

Example 2

Under nitrogen, 7.82 g (50 mmol) of 2-chlorobenzoic acid was combined with 31 g of H$_2$O. 6.62 g (62.5 mmol) of Na$_2$CO$_3$ was then added. The mixture was heated to reflux with stirring for 30 min, remaining under a nitrogen atmosphere. Separately, 36 mg of CuBr and 79 mg of rac-trans-N,N'-dimethylcyclohexane-1,2-diamine (Ligand F) were combined with 1 mL H$_2$O under nitrogen. The resulting mixture was stirred under an air atmosphere until the CuBr was dissolved to give a deep purple solution. This solution was added to the stirred reaction mixture via syringe at 80° C. under nitrogen and stirred for bout 3 h at 100° C. and the reaction was monitored by $^1$H NMR. Table 3 shows the distribution of starting material and product at different reaction times. A product selectivity of more than 99% was observed. After reaction completion, the mixture was allowed to cool to 25° C. and the reaction mixture was acidified with 15% HCl, producing a white precipitate. The white precipitate was filtered, washed with water and dried yielding 6.00 g 2-hydroxybenzoic acid (85% yield). The filtrate was extracted with ethyl acetate and evaporated to dryness to receive another 0.65 g of 2-hydroxybenzoic acid resulting in a total yield of 6.65 g (48.2 mmol, 96% yield).

TABLE 3

| Progress of Example 2 | | | | |
|---|---|---|---|---|
| 2 chlorobenzoic acid | 2-hydroxybenzoic acid | benzoic acid | SEL | Time [min] |
| 17% | 82% | 0% | >99% | 10 |
| 2% | 98% | 0% | >99% | 35 |
| 2% | 97% | 0% | >99% | 65 |
| 1% | 98% | 0% | >99% | 120 |

Example 3

Comparative

Under nitrogen, 7.82 g (50 mmol) of 2-chlorobenzoic acid was combined with 31 g of $H_2O$, generally following the process described in Comdom et al (above). 10.37 g (75 mmol) of $K_2CO_3$, 4.04 g of pyridine (about 51 mmoles), and 0.25 g of copper powder were added and the mixture was heated to reflux with stirring for about 3 h. The reaction was monitored by $^1H$ NMR. Table 4 shows the distribution of starting material and product at different reaction times. A product selectivity of between 82 and 92% was observed depending on reaction time. After reaction completion the mixture was allowed to cool to 25° C. and the reaction mixture was acidified with 15% HCl, producing a white precipitate. The white precipitate was filtered, washed with water and dried yielding 5.60 g of a mixture of 2-hydroxybenzoic acid (74% mol), 2-chlorobenzoic acid (19% mol) and benzoic acid (7% mol). The filtrate was extracted with ethyl acetate and evaporated to dryness to receive another 0.72 g of the same product resulting in a total yield of 6.32 g of crude product. The net yield of 2-hydroxybenzoic acid amounted to 33.6 mmol (67%).

TABLE 4

Progress of Example 3

| 2-chlorobenzoic acid | 2-hydroxybenzoic acid | Benzoic acid | SEL (%) | Time [min] |
|---|---|---|---|---|
| 91% | 7% | 2% | 82 | 10 |
| 84% | 14% | 2% | 88 | 35 |
| 50% | 46% | 4% | 92 | 65 |
| 19% | 74% | 7% | 91 | 120 |

Example 4

Under nitrogen, 2.00 g (9.95 mmol) of 2-bromobenzoic acid was combined with 10 g of $H_2O$. 1.11 g (10.45 mmol) of $Na_2CO_3$ was then added. The mixture was heated to reflux with stirring for 30 min, remaining under a nitrogen atmosphere. Another 1.58 g (14.92 mmol) of $Na_2CO_3$ was added to the reaction mixture and reflux was continued for 30 min. Separately, 14 mg of CuBr and 28 mg of rac-trans-N,N'-dimethylcyclohexane-1,2-diamine (Ligand F) were combined with 1 mL acetonitrile under nitrogen. The resulting mixture was stirred under an air atmosphere until the CuBr was dissolved to give a blue solution. This solution was added to the stirred reaction mixture via syringe at 80° C. under nitrogen and stirred for 2 h at 80° C. After cooling to 25° C., the reaction mixture was acidified with 15% HCl, producing a white precipitate. The white precipitate was filtered and washed with water. After drying, a total of 1.34 g (9.7 mmol, 98% yield) salicylic acid was collected. The purity was determined by $^1H$ NMR to be >99%.

Example 5

Example 5 was carried out using the same procedure as in Example 1 but substituting an equimolar amount of $CuSO_4$ for the $CuBr_2$. After drying, a total of 1.30 g (9.4 mmol, 95% yield) salicylic acid was collected. The purity was determined by $^1H$ NMR to be about 99%.

Examples 6, Example 7

Comparative

Under nitrogen 2 mmol of 2-bromobenzoic acid was stirred with a solution of 3 mmol $Na_2CO_3$ at 80° C. until all of the acid was dissolved. Subsequently, 0.01 mmol of CuBr and either 0.02 mmol of rac-trans-N,N'-dimethylcyclohexane-1,2-diamine (Example 6, Ligand F), or 0.01 mmol of 1,1,4,7,10,10-hexamethyltriethylenetetramine [Example 7 (Comparative), Ligand O] dissolved in 1 mL acetonitrile were added and the reaction mixture was heated at 80 for 3 h. After cooling to ambient temperature the reaction mixtures were carefully acidified with 35% aqueous HCl. The products were isolated by filtration, washed with water and dried under vacuum. The filtrate was extracted with ethyl acetate and evaporated to dryness. The crude reaction products were analyzed by $^1H$ NMR (d6-dmso). The results, summarized in Table 5, demonstrate the poor performance of the tertiary tetraamine [Ligand 0 (Comparative)] in Example 7 in comparison with the N,N'-substituted 1,2-diamine ligand (Ligand F) used in Example 6.

TABLE 5

| | Examples 6 and 7 | | |
| Example | 2-bromobenzoic acid | 2-hydroxybenzoic acid | Net yield |
|---|---|---|---|
| 6 | 0% | >99% | 96% |
| 7 (Comparative) | 95% | <5% | <5% |

Examples 8-23

Under nitrogen, 2 mmol of the halogen-substituted benzoic acid indicated in Table 6 was stirred with a solution of 3 mmol $Na_2CO_3$ at 50-75° C. until all of the halogen-substituted benzoic acid was dissolved. Subsequently, 0.02 mmol $CuSO_4$ and 0.04 mmol rac-trans-N,N'-dimethylcyclohexane-1,2-diamine (Ligand F) dissolved in 1 mL deionized water were added and the reaction mixture was heated at 80-100° C. for 4 h. After cooling to ambient temperature the reaction mixtures were carefully acidified with 35% aqueous HCl.

In isolation method A, the products were extracted from the aqueous layer twice with ethyl acetate, the ethyl acetate fractions were combined and the crude reaction product was isolated by evaporation of ethyl acetate under vacuum. In isolation method B, the products were isolated by filtration, washed with water and dried under vacuum. The crude reaction product was analyzed by $^1H$ NMR (d6-dmso). The results are summarized in Table 6.

TABLE 6

Examples 8–23

| Example | Starting material Halogenated Benzoic Acid | Benzoic Acid Product | T (° C.) | Isolation Method | CONV (%) | SEL (%) |
|---|---|---|---|---|---|---|
| 8 | 2,5-dibromo- | 2-hydroxy-5-bromo- | 80 | B | >99 | >99 |
| 9 | 2-bromo-5-nitro- | 2-hydroxy-5-nitro- | 80 | B | >99 | >99 |
| 10 | 2-bromo-5-nitro- | 2-hydroxy-5-nitro- | 100 | A | >99 | >99 |
| 11 | 2-bromo-5-methyl- | 2-hydroxy-5-methyl- | 80 | B | >99 | >99 |
| 12 | 2-bromo-5-methyl- | 2-hydroxy-5-methyl- | 100 | A | >99 | >99 |
| 13 | 4-bromo- | 4-hydroxy- | 100 | A | >99 | >99 |
| 14 | 4-chloro- | 4-hydroxy- | 80 | B | >99 | >99 |
| 15 | 2,4-dichloro- | 2-hydroxy-4-chloro- | 100 | A | 70 | >99 |
| 16 | 2,5-dichloro- | 2,5-dihydroxy- | 80 | B | 93 | >99 |
| 17 | 2-chloro-5-nitro- | 2-hydroxy-5-nitro- | 100 | A | 74 | >99 |
| 18 | 2-chloro-3,5-dinitro- | 2-hydroxy-3,5-dinitro- | 100 | A | >99 | >99 |
| 19 | 2-chloro-3,5-dinitro- | 2-hydroxy-3,5-dinitro- | 80 | B | >99 | >99 |
| 20 | 2-chloro-5-methyl- | 2-hydroxy-5-methyl- | 100 | A | >99 | >99 |
| 21 | 2-bromo-5-methoxy- | 2-hydroxy-5-methoxy- | 100 | A | >99 | >99 |
| 22 | 2-bromo-5-methoxy- | 2-hydroxy-5-methoxy- | 80 | B | >99 | >99 |
| 23 | 2-chloro-5-bromo- | 2-hydroxy-5-bromo- | 80 | B | 73 | >99 |

Example 24

Under nitrogen, 1.86 g (10.0 mmol) of 2-chloro-4-methylbenzoic acid was combined with 10 g of $H_2O$. 1.11 g (15 mmol) of Ca(OH)2 was then added. The mixture was heated at 85° C. under stirring for 60 min, remaining under a nitrogen atmosphere. Separately, 43 mg of CuBr and 94 mg of rac-trans-N,N'-dimethylcyclohexane-1,2-diamine (Ligand F) were combined with 1 mL deionized water under nitrogen. The resulting mixture was stirred under an air atmosphere until the CuBr was dissolved to give a blue solution. This solution was added to the stirred reaction mixture via syringe at 80° C. under nitrogen and stirred for 24 h at 80° C. After cooling to 25° C., the reaction mixture was acidified with 15% HCl, producing a white precipitate. The white precipitate was filtered and washed with water. After drying, a total of 1.45 g (9.5 mmol, 95% yield) of 2-hydroxy-4-methylbenzoic acid was collected. The purity was determined by $^1$H NMR to be >99%.

Example 25

The same procedure as described in Example 24 was performed but using 2.45 g (10.0 mmol) of 4-bromoisophthalic acid as the substrate and 2.70 g (25.5 mmol) of $Na_2CO_3$ instead of Ca(OH)$_2$. A total of 1.49 g (8.2 mmol, 82% yield) of 4-hydroxyisophthalic acid was collected. The purity was determined by $^1$H NMR to be 88%.

Example 26

The same procedure as described in Example 25 was performed but using 2.01 g (10.0 mmol) of 4-bromobenzoic acid as the substrate and 16 mg of $CuSO_4$ as the copper source. A total of 1.13 g (7.76 mmol, 81% yield) of 4-hydroxy-benzoic acid was collected. The purity was determined by $^1$H NMR to be 90%.

Example 27

The same procedure as described in Example 1 was performed but using 12.25 g (50.0 mmol) of 2-bromo-p-terephthalic acid as the substrate, 31 g of $H_2O$, a total of 9.94 g (94 mmol) of $Na_2CO_3$, 35 mg of CuBr as the copper source and 79 mg of Ligand F. A total of 7.9 g (39 mmol, 78% yield) of 2-hydroxy-terephthalic acid was collected. The purity was determined by $^1$H NMR to be 97%.

Example 28

Under nitrogen, 2.00 g (8.51 mmol) of 2,5-dichloroterephthalic acid was combined with 10 g of $H_2O$. 0.938 g (8.85 mmol) of Na₂CO₃ was then added. The mixture was heated to reflux with stirring for 30 min, remaining under a nitrogen atmosphere. Another 1.31 g (12.34 mmol) of Na₂CO₃ was added to the reaction mixture and reflux was continued for 30 min. Separately, 12 mg of CuBr and 24 mg of rac-trans-N,N'-dimethylcyclohexane-1,2-diamine (Ligand F) were combined with 2 mL H₂O under nitrogen. The resulting mixture was stirred under an air atmosphere until the CuBr was dissolved to give a deep purple solution. This solution was added to the stirred reaction mixture via syringe at 80° C. under nitrogen and stirred for 20 h at 80° C. After cooling to 25° C., the reaction mixture was acidified with HCl (conc.), producing a dark yellow precipitate. The yellow precipitate was filtered and washed with water. After drying, a total of 1.59 g (8.03 mmol, 94% yield) 2,5-dihydroxyterephthalic acid was collected. The purity was determined by ¹H NMR to be 95%.

Example 29

Under nitrogen, 2.00 g (9.95 mmol) of 3-bromobenzoic acid was combined with 10 g of H₂O. 1.11 g (10.45 mmol) of Na₂CO₃ was then added. The mixture was heated to reflux with stirring for 30 min, remaining under a nitrogen atmosphere. Another 1.58 g (14.92 mmol) of Na₂CO₃ was added to the reaction mixture and reflux was continued for 30 min. Separately, 14 mg of CuBr and 28 mg of rac-trans-N,N'-dimethylcyclohexane-1,2-diamine (Ligand F) were combined with 2 mL water under nitrogen. The resulting mixture was stirred under an air atmosphere until the CuBr was dissolved to give a blue solution. This solution was added to the stirred reaction mixture via syringe at 80° C. under nitrogen. The temperature was increased to give a steady reflux and continued to stir for 25 hr. After cooling to 25° C., the reaction mixture was acidified with 15% HCl, producing a white precipitate. The white precipitate was filtered and washed with water. ¹H NMR analysis showed a conversion of 78% with a selectivity of 3-hydroxybenzoic acid of 100%. The overall yield was determined to be 78%.

Examples 30-32

Under nitrogen, 10 mmol of 2-bromobenzoic acid was stirred with a solution of 12.5 mmol Na₂CO₃ in 10 mL H₂O at 50-75° C. until all of the halogen substituted benzoic acid was dissolved. Subsequently, 0.01 mmol copper source (CuBr or CuSO₄ as indicated in Table 7) and 0.02 mmol of either Ligand F or Ligand R (as indicated in Table 7), dissolved under stirring with air in 1 mL deionized water, were added; and the reaction mixture was heated at the temperature and for the time noted in Table 7. After cooling to ambient temperature, the reaction mixtures were acidified with 35% aqueous HCl. The products were isolated by filtration, washed with water and dried under vacuum. The crude reaction product was analyzed by ¹H NMR (d6-dmso). The results are summarized in Table 7.

TABLE 7

| | | Examples 30~32 | | | | | |
|---|---|---|---|---|---|---|---|
| Example | Ligand Code | CONV (%) | SEL (%) | T (° C.) | t (h) | Cu Source | Ligand Structure |
| 30 | R | 3% | >95 | 80 | 3 | CuBr | (2,2'-bipyridine) |
| 31 | F | >99 | >98 | 80 | 3 | CuBr | rac-trans-N,N'-dimethylcyclohexane-1,2-diamine |
| 32 | F | >99 | >98 | 80 | 3 | CuSO₄ | rac-trans-N,N'-dimethylcyclohexane-1,2-diamine |

Examples 33~48; Example 49

Comparative

Under a nitrogen atmosphere, to a 2 mL vial with magnetic stir bar was added 25 mg (0.077 mmol) of 2,5-dibromoterephthalic acid ("DBTA"), followed by 0.308 mL (0.308 mmol) of 1.0 M aqueous sodium hydroxide and 0.169 mL (0.169 mmol) of 1.0 M aqueous sodium acetate. The mixture was then treated with 0.003 mL (0.00077 mol, 1 mol %) of 0.23 M copper(I) bromide in acetonitrile and 0.003 mL (0.00154 mmol, 2 mol %) of the diamine ligand as noted below in Table 8. For Example 50 (Comparative), no ligand was used. The reactor vial was then sealed under nitrogen and placed in a sealed reactor block. After 3 hours at 90° C., the reaction mixture was allowed to cool to room temperature. The reaction mixture was acidified with 15% aqueous HCl, producing a precipitate. The precipitate was filtered and washed with H$_2$O and the dried product was analyzed by $^1$H NMR. Percent conversion of DBTA (II) for each ligand is presented in Table 8. Selectivities for DHTA (I) and the intermediate 2-bromo-5-dihydroxyterephalic acid (VII) are also presented in Table 8.

TABLE 8

Examples 33~49

I

II

VII

| Ligand Code | Example | CONV (II, %) | SEL (VII, %) | SEL (I, %) | Ligand Structure |
|---|---|---|---|---|---|
| A | 33 | >99 | <1 | 84 | 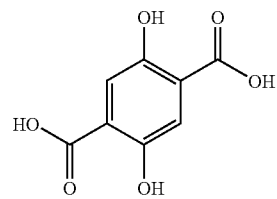 |
| B | 34 | >99 | <1 | 94 | |
| C | 35 | 92 | 5% | 12 | 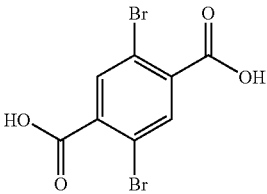 |
| D | 36 | >99 | <1 | 90 | |
| E | 37 | 98 | 4 | 12 | 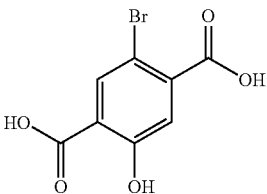 |
| F | 38 | >99 | <1 | >98 | |
| G | 39 | >99 | <1 | 82 | |

TABLE 8-continued

Examples 33~49

I

II

VII

| Ligand Code | Example | CONV (II, %) | SEL (VII, %) | SEL (I, %) | Ligand Structure |
|---|---|---|---|---|---|
| H | 40 | 83 | 9 | 10 | 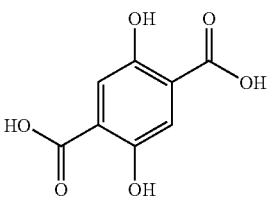 |
| I | 41 | >99 | <1 | 55 | |
| J | 42 | >99 | <1 | 76 | 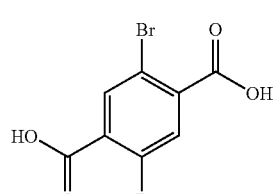 |
| K | 43 | >99 | <1 | 96 | |
| L | 44 | >99 | <1 | 11 | 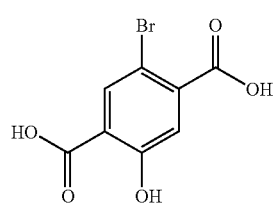 |
| M | 45 | >99 | 2 | 58 | |
| N | 46 | >99 | 3 | 49 | |
| P | 47 | >99 | <1 | 99 | |

TABLE 8-continued

Examples 33~49

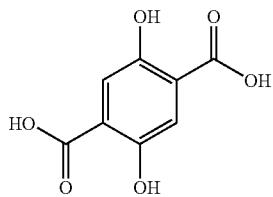 I

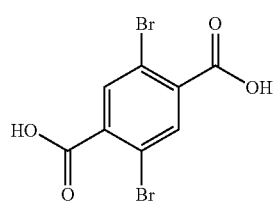 II

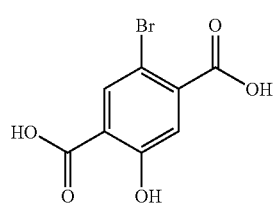 VII

| Ligand Code | Example | CONV (II, %) | SEL (VII, %) | SEL (I, %) | Ligand Structure |
|---|---|---|---|---|---|
| R | 48 | >99 | <1 | 75 | 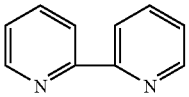 |
| — | 49 (Comparative) | 31 | 32 | 2 | No ligand (Comparative) |

Where an embodiment of this invention is stated or described as comprising, including, containing, having, being composed of or being constituted by certain features, it is to be understood, unless the statement or description explicitly provides to the contrary, that one or more features in addition to those explicitly stated or described may be present in the embodiment. An alternative embodiment of this invention, however, may be stated or described as consisting essentially of certain features, in which embodiment features that would materially alter the principle of operation or the distinguishing characteristics of the embodiment are not present therein. A further alternative embodiment of this invention may be stated or described as consisting of certain features, in which embodiment, or in insubstantial variations thereof, only the features specifically stated or described are present.

Where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

Where a range of numerical values is recited herein, unless otherwise stated, the range is intended to include the endpoints thereof, and all integers and fractions within the range. It is not intended that the scope of the invention be limited to the specific values recited when defining a range.

What is claimed is:

1. A process for preparing an n-alkoxy aromatic acid from a hydroxy aromatic acid that is described generally by the structure of Formula I $$(COOH)_m\text{—}Ar\text{—}(OH)_n \qquad I$$

wherein Ar is a $C_6$~$C_{20}$ arylene radical, n and m are each independently a nonzero value, and n+m is less than or equal to 8, comprising the steps of
   (a) contacting a halogenated aromatic acid that is described generally by the structure of Formula II, $$(COOH)_m\text{—}Ar\text{—}(X)_n \qquad II$$

wherein each X is independently Cl, Br or I, and Ar, n and m are as set forth above, with a base in water to form therefrom the corresponding m-basic salt of the halogenated aromatic acid in water;
   (b) contacting the m-basic salt of the halogenated aromatic acid with a base in water, and with a copper source in the presence of an amine ligand that coordinates to copper, to form the m-basic salt of a hydroxy aromatic acid from the m-basic salt of the halogenated aromatic acid at a solution pH of at least about 8, wherein the ratio of molar equivalents of ligand to molar equivalents of hydroxy aromatic acid is less than or equal to about 0.1, and the ligand comprises, when it is a tetramine, at least one primary or secondary amino group;
   (c) optionally, separating the m-basic salt of the hydroxy aromatic acid from the reaction mixture in which it is formed;
   (d) contacting the m-basic salt of the hydroxy aromatic acid with acid to form therefrom an n-hydroxy aromatic acid; and
   (e) converting the n-hydroxy aromatic acid to an n-alkoxy aromatic acid.

2. A process according to claim 1 wherein the n-hydroxy aromatic acid is contacted under basic conditions with a dialkyl sulfate of the formula $R^9 R^{10} SO_4$ wherein $R^9$ and $R^{10}$ are each independently a substituted or unsubstituted $C_{1-10}$ alkyl group.

3. A process for preparing a compound, monomer, oligomer or polymer from a hydroxy aromatic acid that is described generally by the structure of Formula I $$(COOH)_m\text{—}Ar\text{—}(OH)_n \qquad I$$

wherein Ar is a $C_6$~$C_{20}$ arylene radical, n and m are each independently a nonzero value, and n+m is less than or equal to 8, comprising the steps of
   (a) contacting a halogenated aromatic acid that is described generally by the structure of Formula II, $$(COOH)_m\text{—}Ar\text{—}(X)_n \qquad II$$

wherein each X is independently Cl, Br or I, and Ar, n and m are as set forth above, with a base in water to form therefrom the corresponding m-basic salt of the halogenated aromatic acid in water;
   (b) contacting the m-basic salt of the halogenated aromatic acid with a base in water, and with a copper source in the presence of an amine ligand that coordinates to copper, to form the m-basic salt of a hydroxy aromatic acid from the m-basic salt of the halogenated aromatic acid at a solution pH of at least about 8, wherein the radio of molar equivalents of ligand to molar equivalents of hydroxy aromatic acid is less than or equal to about 0.1, and the ligand comprises, when it is a tetraamine, at least one primary or secondary amino group;

(c) optionally, separating the m-basic salt of the hydroxy aromatic acid from the reaction mixture in which it is formed;

(d) contacting the m-basic salt of the hydroxy aromatic acid with acid to form therefrom an n-hydroxy aromatic acid; and (e) subjecting the n-hydroxy aromatic acid to a reaction to prepare therefrom a compound, monomer, oligomer or polymer.

4. A process according to claim 3 wherein a polymer prepared comprises a pyridobisimidazole-2,6-diyl(2,5-dihydroxy-p-phenylene) polymer.

5. A process according to claim 1 further comprising a step of subjecting the n-alkoxy aromatic acid to a reaction to prepare therefrom a compound, monomer, oligomer or polymer.

6. A process according to claim 1 wherein, in steps (a) and (b), a total of about n+m+1 normal equivalents of water-soluble base are added to the reaction mixture per equivalent of the halogenated aromatic acid.

7. A process according to claim 1 wherein the copper source comprises Cu(O), a Cu(I) salt, a Cu(II) salt, or a mixture thereof.

8. A process according to claim 1 where the ligand comprises a monoamine, diamine, triamine or a tetraamine.

9. A process according to claim 1 where the ligand comprises an N,N'-substituted diamine or a cyclohexyl diamine.

10. A process according to claim 1 wherein the ligand comprises a cyclic amine.

11. A process according to claim 1 wherein copper is provided in an amount of between about 0.1 and about 5 mol % based on moles of halogenated aromatic acid.

12. A process according to claim 1 wherein the ligand is provided in an amount of between about one and about two molar equivalents per mole of copper.

13. A process according to claim 3 wherein, in steps (a) and (b), a total of about n+m+1 normal equivalents of water-soluble base are added to the reaction mixture per equivalent of the halogenated aromatic acid.

14. A process according to claim 3 wherein the copper source comprises Cu(O), a Cu(I) salt, a Cu(II) salt, or a mixture thereof.

15. A process according to claim 3 wherein the copper source is selected from the group consisting of CuCl, CuBr, CuI, $Cu_2SO_4$, $CuNO_3$, $CuCl_2$, $CuBr_2$, $CuI_2$, $CuSO_4$, $Cu(NO_3)_2$, and mixtures thereof.

16. A process according to claim 3 where the ligand comprises a monoamine, diamine, triamine or a tetraamine.

17. A process according to claim 3 where the ligand comprises an N,N'-substituted diamine or a cyclohexyl diamine.

18. A process according to claim 3 wherein the ligand comprises a cyclic amine.

19. A process according to claim 3 wherein copper is provided in an amount of between about 0.1 and about 5 mol % based on moles of halogenated aromatic acid.

20. A process according to claim 3 wherein the ligand is provided in an amount of between about one and about two molar equivalents per mole of copper.

* * * * *